(12) United States Patent
Ho et al.

(10) Patent No.: US 7,909,465 B2
(45) Date of Patent: Mar. 22, 2011

(54) CHARACTERISING EYE-RELATED OPTICAL SYSTEMS

(75) Inventors: Arthur Ho, Coogee (AU); Brien Anthony Holden, Kensington (AU); Klaus Ehrmann, Manly (AU)

(73) Assignee: Brien Holden Vision Institute, Sydney, New South Wales (AU)

( * ) Notice: Subject to any disclaimer, the term of this patent is extended or adjusted under 35 U.S.C. 154(b) by 0 days.

(21) Appl. No.: 12/593,543

(22) PCT Filed: Mar. 28, 2008

(86) PCT No.: PCT/AU2008/000434
§ 371 (c)(1),
(2), (4) Date: Apr. 15, 2010

(87) PCT Pub. No.: WO2008/116270
PCT Pub. Date: Oct. 2, 2008

(65) Prior Publication Data
US 2010/0225883 A1 Sep. 9, 2010

(30) Foreign Application Priority Data

Mar. 28, 2007 (AU) ................................ 2007901634

(51) Int. Cl.
*A61B 3/10* (2006.01)
*A61B 3/00* (2006.01)
(52) U.S. Cl. ........................................ 351/221; 351/246
(58) Field of Classification Search .................. 351/205, 351/211, 221, 246
See application file for complete search history.

(56) References Cited

U.S. PATENT DOCUMENTS

| 5,532,771 A | 7/1996 | Johnson et al. |
| 6,409,345 B1 | 6/2002 | Molebny et al. |

(Continued)

FOREIGN PATENT DOCUMENTS

WO   WO 2005/102418 A1   11/2005

OTHER PUBLICATIONS

Atchison "Coparison of Peripheral Refractions Determined by Different Instruments." Optometry and vision Science, vol. 80, No. 9, Sep. 2003, pp. 655-660.

(Continued)

*Primary Examiner* — Jack Dinh
(74) *Attorney, Agent, or Firm* — Merchant & Gould P.C.

(57) ABSTRACT

An instrument and method for characterizing eye-related optical systems, including the live human eye involves scanning an illuminating light beam from a light source and light detector unit from element to element of a beam deflector array of elements arranged laterally across the optical axis of eye. At each successive element the illuminating beam is deflected to form an interrogating beam that is directed into the eye at a peripheral angle that depends upon the lateral location of the deflector element. A return beam is reflected or back-scattered from the cornea and returned via the same deflector element to the light source and detector unit. This allows the interrogating beams to be scanned sufficiently rapidly into the eye to greatly reduce the variation of eye fixation and gaze that accompany other methods of measuring peripheral refraction or aberration of a natural eye. In addition to or instead of scanning the illuminating beam over each element of the array, all or multiple elements of the array can be illuminated simultaneously and the multiple interrogating rays thus generated can be gated by the use of an LCD aperture plate. Alternatively, an LCD aperture plate can be interposed between a wide illuminating beam and operated to selectively illuminate the beam deflector.

21 Claims, 6 Drawing Sheets

U.S. PATENT DOCUMENTS

| | | |
|---|---|---|
| 6,439,720 B1 | 8/2002 | Graves et al. |
| 6,634,750 B2 | 10/2003 | Neal et al. |
| 2005/0163455 A1 | 7/2005 | Polland |
| 2005/0203422 A1 | 9/2005 | Wei |

OTHER PUBLICATIONS

Atchison. "Recent advances in measurement of monochromatic aberrations of human eyes." Clinical and experimental Optometry, vol. 88, Jan. 1, 2005, pp. 5-27.

Artal. "Refraction, Aliasing, and the Absence of Motion Reversals in Peripheral Vision." Vision Research, vol. 35, No. 7, pp. 939-947, 1995.

Gustafsson et al. "Peripheral astigmatism in emmetropic eyes." Opthal. Physiol. Opt. vol. 21, No. 5, pp. 393-400, 2001.

Gwiazda et al. "Comparison of Spherical Equivalent Refraction and Astigmatism Measured with Three Different Models of Autorefractors." Optometry and Vision Science, vol. 81, No. 1, Jan. 2004, pp. 56-61.

Schmid "Axial and peripheral eye length measured with optical low coherence reflectometry." Journal of Biomedical Optics, vol. 8, No. 4, Oct. 2003, pp. 655-662.

Webb "Measurement of ocular local wavefront distortion with a spatially resolved refractometer." Applied Optics, vol. 31, No. 19, Jul. 1, 1992, pp. 3678-3686.

Schmid, G. et al. "Measurement of eye length and eye shape by optical low coherence", International Ophthalmology, vol. 23, 2001, pp. 317-320.

CHARACTERISING EYE-RELATED OPTICAL SYSTEMS

This application is a National Stage Application of PCT/AU2008/000434, filed 28 Mar. 2008, which claims benefit of Serial No. 2007901634, filed 28 Mar. 2007 in Australia and which applications are incorporated herein by reference. To the extent appropriate, a claim of priority is made to each of the above disclosed applications.

BACKGROUND OF THE INVENTION

1. Technical Field

This invention relates to methods, instruments and apparatus for optically characterising eye-related optical systems, preferably over wide angles of view. Eye-related optical systems include the natural animal eye, alone or in association with prosthetic lenses and with or without surgical or other modification. They also include physical eye models or simulated eyes with or without modification to simulate optical disorders and/or corrective measures.

Optical characterisation typically involves refractometry; that is, the determination of the optical power of portion or the entire optical path traveled by an interrogating ray and it may, for example, include mapping—or spatially resolving—refractive power over an area or surface of the eye-related system, which is sometimes referred to as wavefront aberrometry. Optical characterization may also include determination of the length of the eye-related system, for example the distance from the anterior surface of the cornea to the anterior surface of the retina. Other characteristics of natural eyes, such as the profile and thickness of the cornea, pupil size and the depth of the anterior chamber, may also be important for certain surgical procedures (eg, lens replacement or ablative laser treatment) but are not of prime concern in this invention.

Of particular—but not exclusive—interest are methods and instruments suitable for use by optometrists in determining the peripheral refraction—and, optionally, the length—of the human eye for the purpose of prescribing anti-myopia treatment. Peripheral angles of 20-30 degrees with respect to the optic axis are of particular interest in this respect, with angles up to about 40 degrees also being relevant. Even higher peripheral angles are of research interest to specialists.

2. Description of Related Art

Several methods and instruments have been used to measure central refraction errors and aberrations of the eye. Refractive error is a subset of the total aberration of the eye and traditionally expressed in terms of sphere and cylinder components along with the orientation of the cylinder axis. Although it is possible to extract the refractive error, also called lower order aberrations, from the measurements of total aberration, the instruments used in clinical practice are usually dedicated to either measurement of refractive error or total aberration. While neither instrument is designed for measurement of peripheral refraction or aberration, commercial instruments have been modified to obtain measurements of peripheral refraction for both the accommodated and unaccommodated eye. The modifications include some form of off-centre fixation with and head or eye movement being needed.

Atchinson [Atchinson D A. "Comparison of peripheral refractions determined by different instruments". Optom Vis Sci 2003; 80:655-60] describes one such comparison of two auto-refractometers (Canon Autoref R-1 and Shin-Nippon SRW-5000) and one Hartmann-Shack wavefront aberrometer. With all three instruments, peripheral refraction or total aberration was measured by rotating and fixating the eye on a series of fixation targets along the horizontal meridian of up to 40° nasal and temporal. All measurements were taken sequentially, with patients being instructed to fixate on a particular target and then re-centering the pupil position with the optical axis. Overall, the three instruments produced similar results, although the Canon results are more variable. Several similar investigations have been published using similar methods and instruments and obtaining similar results. [Gwiazda J, Weber C. Comparison of spherical equivalent refraction of astigmatism measured with three different model of autorefractors. Optom Vis Sci 2004; 81:56-61, and Gustafsson J, Terenius E, Buchheister J, Unsbo P. Peripheral astigmatism in emmetropic eyes. Ophthalmic Physiol Opt 2001; 21:393-400.]

A number of different optical methods have been utilised to automatically determine the refractive status of the live eye. The basic principle employed is the projection of an optical pattern or beam onto the retina and the analysis of the reflected pattern. An overview of these methods is given in [Atchinson D A. "Recent advances in measurement of monochomatic aberrations of human eyes". Clin Exp Optom 2005; 88: 1: 5-27]. One of the most commonly used principles is used in the Shin-Nippon SRW-5000 instrument in which an infrared ring target is projected onto the retina and the reflected image is captured with a CCD camera. A lens relay system moves rapidly, scanning through the focus range and the size of the images are analysed in multiple meridians to provide the data from which the aberrations (including refraction) can be derived. Some of these techniques have the advantage of being 'open-field' in that the subject can look through a glass window and semi silvered mirror into the distance, thus preventing instrument myopia, but also allowing fixation at off axis angles. Typically, the angular fixation range is limited to less than 30° in the horizontal and about half of that in the vertical meridian. This technique is not sufficient to fully characterize peripheral aberration with and without vision correction devices.

A similar instrument was described and used in a laboratory setting by Artal et al. [Artal P, Derrington A M, Colombo E. "Refraction, aliasing, and the absence of motion reversals in peripheral vision". Vision Res 1995; 35: 939-47.] A point image is projected onto the retina. The reflected image is observed with a CCD camera while moving the 'focusing block' axially until the best focus position with smallest circle of confusion was found. To assess astigmatism, the positions for sharpest horizontal and vertical profiles were also determined. A fixation target was placed at comfortable viewing distance in locations for 15°, 20° and 40° retinal eccentricities in the horizontal meridian.

Webb et al describe a modified Scheiner system whereby the subject manipulates the incidence angle of one of the Scheiner beams until two dots on the retina merge into one. [Webb R H, Penney C M, Thompson K R "Measurement of ocular local wavefront distortion with a spatially resolved refractometer". Appl Opt 1992; 31: 3678-3686.] Although the measurement beam enters the pupil non-parallel to the optical axis, the angular deviations are very small and only compensate the paraxial wavefront error of the eye. No peripheral refraction measurements appear possible with this system.

In 2003, Schmid presented results of peripheral axial length measurements from an instrument developed utilising optical low coherence reflectometry. [Schmid G F. "Axial and peripheral eye length measured with optical low coherence reflectometry". J. Biomed. Opt. 2003 8(4): 655-662. See also, Schmid et al, "Measurement of eye length and eye shape by optical low coherence reflectometry". Intnl. Opth. 2001 23(4-6).] A fixation LED was coupled into the central optical path to keep the eye aligned with the optical axis of the instrument. A beam steering mirror deflects the measurement beam horizontally and vertically by up to 15° for off-axis measurements. The measurement principle requires the incident beam to be aligned perpendicular to the cornea at the point of intersection. Due to the non-spherical shape of the cornea, small lateral repositioning of the instrument is necessary for each new incident angle. This manual process prohibits rapid measurements across the angular range.

In U.S. Pat. No. 6,439,720, Graves et al disclose an instrument for measuring lower and higher order aberrations of the human eye. The method described is one of several variations of double pass techniques, whereby a probing light beam illuminates a spot on the retina and the reflected wavefront is analysed after exiting the eye. In this patent, a pair of Littrow prisms is used to split the emerging light ray into two parallel beams which pass through a moveable collimating lens to generate two slightly defocused images on a CCD detector. From the two computer analysed images, the ocular aberrations can be determined. The patent describes only on axis measurements of lower and higher order aberrations.

Wei et al [US patent 20052034] disclose a multifunctional instrument to measure axial eye length and corneal topography. Although not directly dedicated to obtain aberration and refraction results, the instrument features several sub-components also used in aberrometry and the combination of axial length parameters and keratometry data allows some estimation of the refractive status. Again, the instrument is designed for on axis measurements only. The fixation target can be moved but only along the optical axis to stimulate different accommodative responses.

An instrument to measure aberrations of the eye at a plurality of locations was disclosed by Molebny at al [U.S. Pat. No. 6,409,345]. The plurality of locations are achieved by parallel offsetting the probing light beam with respect to the optical axis. Aberration mapping is thus confined to paraxial scanning to obtain power maps across the entrance pupil. As with Wei et al (above), a fixation target is added to align the optical axis and to control accommodation.

The techniques outlined above are generally unsatisfactory because the patient is unable to correctly fixate gaze for the time needed and because the peripheral angle at which the measurement is taken is difficult to measure with accuracy or reliability. Attempting to map peripheral power even over a few spots on the eye in one sitting is impractical and repeatability between different sittings is generally poor.

Neal et al [U.S. Pat. No. 6,634,750] disclose a 'tomographic wavefront analysis system and method of mapping an optical system' in which interrogating beam(s) are scanned into multiple locations within the eye and back-scattered light from is detected and processed into an aberration map or representations of the three-dimensional structure of the eye using computer automated tomography. While the difficulty of peripheral gaze fixation is avoided, the system is highly complex, unsuited for use in normal optometry practise and appears to be incapable of interrogating an eye at peripheral angles greater than about 10-15 degrees with respect to the optic axis. Further, the disclosed technique is only suited to the use of spot beams and does not envisage or permit the use of interrogating beams having various cross-sectional shapes, such as squares, circles, ellipses or rings which assist in auto focussing/ranging and accelerate wavefront analysis.

Methods and instruments that are capable of more accurate peripheral refraction measurements over wide peripheral angles are needed to provide important inputs for the determination of ocular shape, eye length or retinal contour. Such inputs are now of significant interest in the study and treatment of eye pathologies such as progressive myopia.

BRIEF SUMMARY OF THE INVENTION

The present invention involves use of an array of discrete beam deflector elements that extends laterally from the optical axis of the eye-related system and from which elements interrogating beams can be directed into the eye-related system over a wide range of peripheral angles. These interrogating beams in turn generate return beams from within the eye-related system that are transmitted to detector means via the same beam deflector elements. The interrogating beams can be generated by illuminating elements of the array with an illuminating beam or beams that may be scanned over the array. The scanning preferably takes place from a common point so that all return beams are returned to that source for detection by a single detector. Refractive error and other aberrations of the eye-related system can be determined and, if desired, mapped onto a surface of the system, by comparing the interrogating beam with the returned beam for each element of the array. This may be done by comparison of wavefronts, relative displacement, angle, position or cross-sectional shape. Since the source, illumination and interrogation beams will have substantially identical optical properties, it will be convenient to use the source beam as a proxy for the interrogation beam in such comparisons. Indeed, it will normally be sufficient to store data concerning the source beam as a basis for such comparisons. Reference to comparing the return beam with the interrogating beam should therefore take this into account.

The beam deflector array may extend on one side or both of the optical axis, be straight or curved, cruciform, star, disc, dish or line shaped. For simplicity and convenience, a line or linear array (straight or curved) that extends equally on each side of the axis is preferred as it allows a complete meridian of the eye to be assessed with one setting of the array. A linear array, whether extending to one or both sides of the axis, can be rotated to cover all meridians and polar angles. Each deflector element of the array functions to (i) deflect an illuminating beam from a light source as an interrogation beam into the eye-related system and to (ii) deflect the reflected or back-scattered return beam to the detector means. The angle of the interrogating beam relative to the optical axis is determined both by the nature of the beam deflector element (eg, fixed or steerable prisms or mirrors) and its lateral location in the array. More remote deflector elements normally give rise to larger interrogation angles. In this way, peripheral angles up to and in excess of 40 degrees can be readily scanned, with angles of between 20 and 30 degrees normally being adequate for characterising myopic eyes for corrective therapy. A deflector element may be moveable from location to location within the array to cover multiple angles but the added complication and inaccuracies are not likely to make this worthwhile. Preferably, therefore the beam deflector elements occupy fixed positions in the array, though it is envisaged that individual elements may be tiltable under processor control to adjust the angle of their interrogation beams. Preferably, however, a source light beam is scanned sequentially from a common point over the deflector elements and each return beam is returned via each element as it is scanned to the common point.

It is preferable to generate the interrogation beams one at a time so that the total intensity of the light entering a human eye being examined at any instant is minimised. This also enhances the ability of the detector means to discriminate between returned beams. However, scanning an illuminating beam from one array element to the next is not essential as sequential generation of interrogation beams can be achieved in other ways—by the use of electronic shutters before and/or behind the array or by use of moveable beam deflector elements, for example. With any of these, a rapid sequence of interrogating beams can be generated over a wide range of interrogation angles, the speed of scan being largely determined by the rate at which return beams can be detected and the associated data recorded. Scanning and detection are preferably conducted automatically by or under the control of a PC or other digital processor/controller.

Rapid scanning is highly desirable to allow good fixation of a live natural eye throughout the procedure, it being preferred that the entire interrogation and detection sequence take place over a period of a few seconds. Preferably the subject is asked to fixate gaze upon an on-axis target and, when fixation is confirmed, the scan sequence is initiated automatically. Optimally, the technique allows optical characteristics of the eye-related system to be computed and mapped substantially in real-time.

Where scanning is thought to be speed-limiting, a few beam deflection elements may be illuminated at once to generate multiple simultaneous return beams that will need to be distinguished for separate detection. This can be done by using the aforementioned electronic shutters to chop or pulse-code one or more of the return beams. Selective polarisation may also be employed to distinguish the return beams, which can also be implemented by a suitable electronic shutter serving as a selective polariser.

Because an interrogating beam will encounter multiple interfaces between materials of different optical characteristics as it travels into the eye-related system, the respective returned beam will be composed of a set of component returned beams. The component returned beam which is generally of most interest is that returned from the retina (the rear-most interface of the eye-related system) because this provides the longest beam path in the eye. Fortunately, the component beams returned from the cornea and retina are also usually the most intense and/or distinct. While component beams returned from other surfaces within the eye-related system are more difficult to detect and distinguish from one another, the technique of the present invention allows for such component returned beams to be selected for analysis. Selection and comparison of return beam components associated with both the cornea and the retina will allow the length of the eye to be determined using interferometric methods, eye length being of critical interest for the monitoring of myopia progression.

Interferometric measurement of eye length may be combined with the mapping of refractive aberrations of an eye with particular advantage where a scanning illuminating beam is generated from a source beam at a single or common point, as by the use of a moving mirror scanner. This allows each return beam with its retina and cornea components to be returned to a common location where aberrations and cornea-retina distance can be determined for every return beam. The common location is the source beam prior to the scanning point where the return beams can be coupled into a detector beam path and an interferometer beam path using beam-splitters. To measure retina-cornea distance, a reference beam (part of the source beam) is also coupled into the interferometer beam path so that it can interfere with the return beam components in a manner that can be detected, interference being created by changing the length of the interferometer beam path in such a way that the length of the reference beam relative to the return beam in that path is changed. This change in length can be effected by moving a mirror and monitoring for interference, the distance the mirror moves being related to the retina-cornea distance, though not identical. To achieve interference in this way the reference beam (and therefore the source beam) is preferably of low coherence, substantially monochromatic and preferably in the near infra-red.

From one aspect, the invention is concerned with a method for optically characterising an eye-related optical system involving, illuminating a beam deflector element in an array that extends laterally from the optical axis to generate an interrogating light beam that is directed into the eye-related system at a predetermined angle relative, detecting a reflected or back-scattered return beam from the eye-related system that is returned via the illuminated beam deflector element, and comparing the returned beam with the interrogating, illuminating or source beam to determine wavefront differences indicative of aberrations of the eye-related optical system at the predetermined angle.

From another aspect, the invention is concerned with an instrument based on the above method that includes an array of beam deflector elements extending from the optical axis, means for illuminating the array to generate the interrogation beams and means for detecting the returned beams and comparing them with the undistorted interrogation, illuminating or source beam, all of which can be assumed to be free of aberrations or at least to have calibrated aberrations. Typically, the source beam—and therefore the illuminating beams, the interrogating beams and the return beam—will be of narrow spectral width within the visible or infra-red region, near infra-red being preferred as noted above.

From another aspect, the method of the invention may employ a laterally extending array of beam deflector elements to generate interrogating beams that are directed sequentially into a subject eye at peripheral angles, using the deflector elements of the array to direct light returned from the eye from each interrogating beam to common detector means as a sequence of returned beams, differencing the wavefronts of each interrogating beam and its respective returned beam to determine the refractive power of the eye along the path of that interrogating beam and return beam within the eye.

The terms 'in front of' and 'behind', and 'forwards' and 'rearwards' are used to indicate relative disposition with respect to the eye-related system. Thus, the array of beam deflector elements (where employed) will be located in front of the eye-related system, the interrogation beam will travel rearwards from the array into the eye-related system and the returned beams will travel forwards to the array.

DETAILED DESCRIPTION OF EXAMPLES

Having portrayed the nature of the present invention, particular examples will now be described with reference to the accompanying drawings. However, those skilled in the art will appreciate that many variations and modifications can be made to the examples without departing from the scope of the invention as outlined above.

Figure 1:
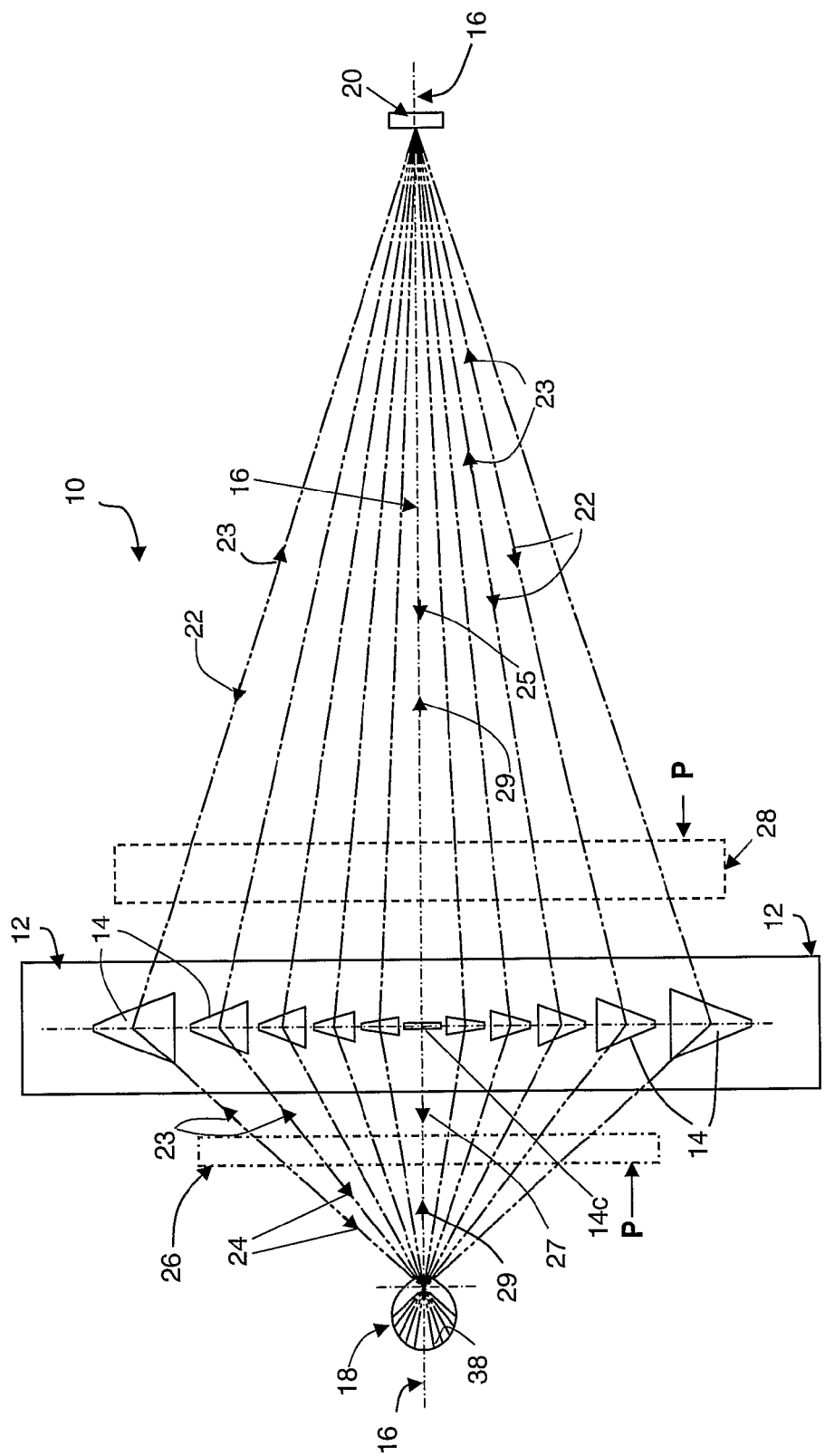
FIG. 1 is a basic diagrammatic plan of the basic optical layout of the first example of an instrument formed in accordance with the present invention in which the deflector means comprises and array of prisms.

The basic layout of the instrument 10 of the first example is shown diagrammatically in FIG. 1. The array 12 of deflector elements 14, in this case is a linear row that extends symmetrically and laterally on either side of the optical axis 16 of the eye-related optical system 18 under investigation. It will be assumed that system 18 is the eye of a patient with or without the addition of prosthetic lenses or other modifications. An illuminating light source, controlling processor and return-beam detector are indicated by a single undifferentiated unit 20 arranged on axis 16, which is described in more detail with reference to FIG. 3. Unit 20 directs illuminating beams, indicated by arrow heads 22, to array elements 14 to generate a corresponding set of interrogating beams, indicated by arrow heads 24, that are directed into eye-system 18 at different peripheral angles relative to axis 16. A return beam, indicated by arrow heads 23, is generated by each interrogating beam 24 and is directed back to unit 20 via the respective element 14 for detection. It is convenient for illuminating beams 22 to be directed in sequence from one element 14 to the next to thereby sequentially generate the interrogating beams 24 and return beams 23.

In this example, a central illuminating beam, a corresponding central interrogation beam and a corresponding central return beam are indicated by arrow heads 25, 27 and 29. Also in this example, each deflector element is a prism (except central element 14c) that has an apex angle such that each interrogation beam 24 is directed into eye 18 and each return beam 23 is directed to unit 20. Central element 14c is effectively a null element that does not deflect the illuminating beam; it may be a parallel-sided plain glass as shown, but that is not even necessary. Also in this example, array 12 is substantially linear so that interrogating beams 24 and 27 are substantially co-planar allowing one meridian—the horizontal in this example—of system 18 to be investigated. Non-horizontal meridians of the system can be investigated by simply rotating the instrument 10 about optic axis 16 relative to eye 18.

The transmission of interrogating beams 24 and 27 one at a time into eye 18, and the generation of a corresponding sequence of return beams 23 and 29, can be effected in a variety of ways. First (as will be described below), unit 20 may include a beam scanner that directs a single narrow illuminating beam from one element 14 to another. Second, multiple elements 14 can be illuminated at one time and interrogating beams 24 and 27 can be gated to effect scanning of eye 18 and the generation of a sequence of return beams 23 and 25, This can be done by, for example, inserting an electronically controllable LCD shutter 26 between array 12 and eye 18 and using it as scanning means by which interrogating beams 24 from prisms 14 are admitted into eye 18 one at a time. Third, a similar shutter 28 may be inserted between array 12 and unit 20 to gate illuminating beams 22 and 25 to illuminate one or more elements 14 at a time. Thus, it is not essential for unit 20 to include scanning means and it is possible to distribute the scanning function between scanner means in unit 20 and shutters such as indicated at 26 and/or 28

In this way, successive interrogation/return beam pairs diverge/converge at successively larger/smaller angles with respect to axis 16 as they pass into and out of eye 18. Sequential scanning from one angle to the next adjacent will probably be most convenient but many other scan sequences may be used to minimise biases that might arise due to fixed sequential scanning. While illumination of more than one beam deflector element 14 at a time can easily be achieved by use of a scanner in unit 20, it is then necessary to distinguish the multiple simultaneous return beams that will result. This can be done by using shutter 26 or 28 as a beam-chopper or selective polariser to differentially encode each return beam that needs to be distinguished from another at the detector.

Figure 2:
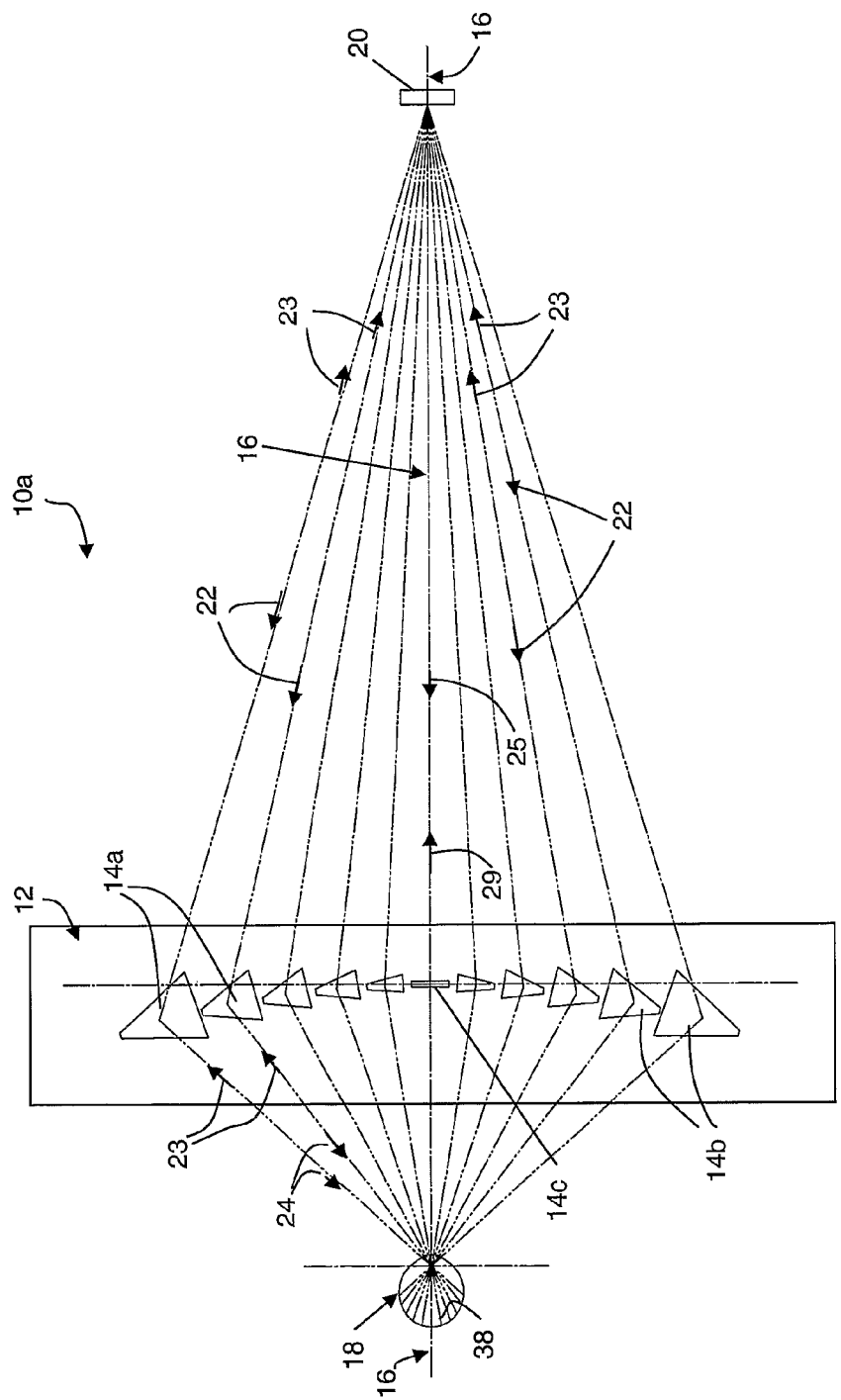
FIG. 2 illustrates one possible modification to the example of FIG. 1 wherein the prisms comprising the deflector array are tilted and arranged in an arc.

A second variant of the instrument of FIG. 1 is illustrated in FIG. 2 and this instrument is indicated at 10a. In this variant the prisms 14a that comprise deflector elements of array 12 are arranged in a curve or arc (rather than being coplanar) and are tilted relative to the corresponding prisms of FIG. 1 so that entry and exit angles of the light beams are equal. Such an arrangement can offer improved performance depending upon the lateral dimensions of the array and the number of deflector elements therein.

Figure 3:
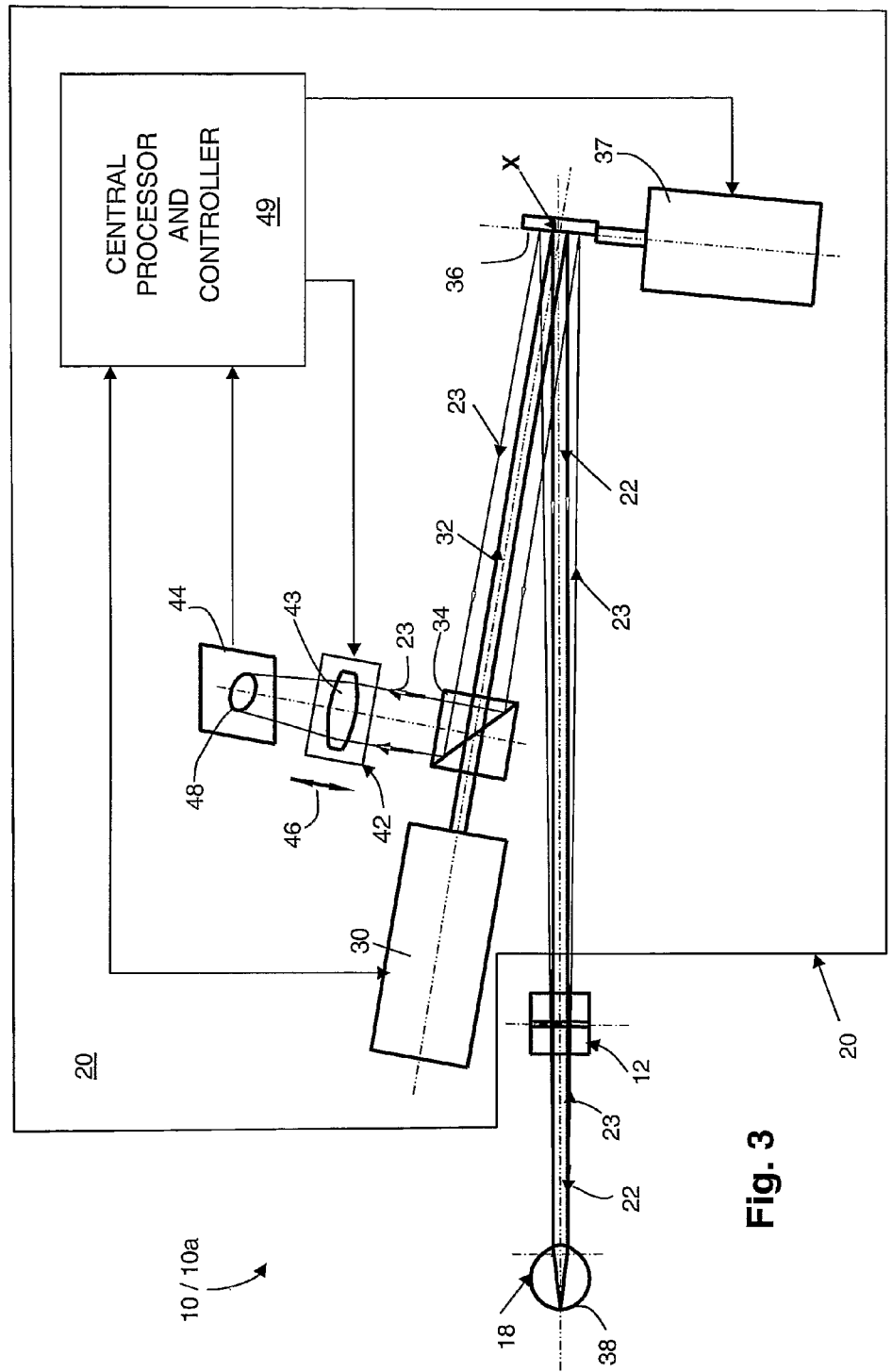
FIG. 3 is an enlarged and more detailed diagrammatic side elevation of the optical layout of the instrument of FIG. 1.

FIG. 3 is a more detailed side elevation of instrument 10 of FIG. 1 or the variant 10a of FIG. 2 in which the principal components of unit 20 are shown separately. A light source 30 directs a collimated source beam 32 via a beam-splitter 34 to an oscillating mirror scanner 36 that is moved by actuator 37 to generate illuminating beams 22 that are scanned from deflector to deflector in array 12 to generate the sequence of interrogating beams 24 that are directed into eye-system 18 and onto the retina 38 over the desired range of incident angles. Scanning mirror 36 thus forms a point source or common point for beams 24 and a common point (indicated at X) for all return beams. Thus, each return beam 23 returned from retina 38 passes back via deflector array 12 and scanner mirror 36 to beam-splitter 34 by which it is diverted via a focusing system 42 to a photo detector 44. System 42 includes a moveable lens assembly 43 that can be moved axially back and forth through a focus range, as indicated by arrows 46. While the source beam 32 (and, thus, the illuminating, interrogating and return beams 22, 24 and 23) can have any desired spot, disc or annular cross-section desired, an annular cross-section like that commonly used in known autorefractors (such the Shin-Nippon SRW-5000 mentioned above) is preferred as it can be analysed and processed in a substantially standard manner.

Each return beam 23—or more correctly its image 48 at detector 44—thus contains information of the refractive status of the eye-system that is captured or quantified by detector 44, which is preferably a two-dimensional array of photo sensors.

Finally, unit 20 includes a central processor and controller 49 that may conveniently comprise a dedicated PC and is connected to accept and analyse the output of detector 44 and to drive lens assembly 43 under servo-control. Processor 49 is also connected to control scanner driver 37 and to ensure correct timing of illumination and return signal detection. A connection between light source 30 and processor 49 is also shown as it will be convenient to ensure that source beam 32 is correctly configured and that a representation of the current source beam sectional pattern is stored for comparison with image 48.

While each return beam 23 is being received, focusing lens assembly 42 is moved along the direction of the optical axis to vary the focus size and shape of the image 48. Commonly, three positions of the focussing assembly 42 are recorded for each of three return beam image shapes: one position where the image (spot or ring) appears smallest and in sharpest focus, a second position where the image appears maximally elongated in one meridian and a third position where the image is maximally elongated in a different meridian, usually one that is orthogonal to the first meridian. The three positions of lens assembly 42 respectively indicate the spherical equivalent power of the eye, the sagital astigmatic component and the tangential astigmatic component of the refraction. The significance of spot/image size in relation to spherical equivalent power of eye 18 can be understood in the following elementary way. Since the interrogating beam 24 that enters eye 18 is collimated, a normal or emmetropic eye will return a parallel collimated beam, a myopic eye will return a convergent beam and a hyperopic eye will return a divergent beam, both of which will result in larger images sizes.

Figure 4:
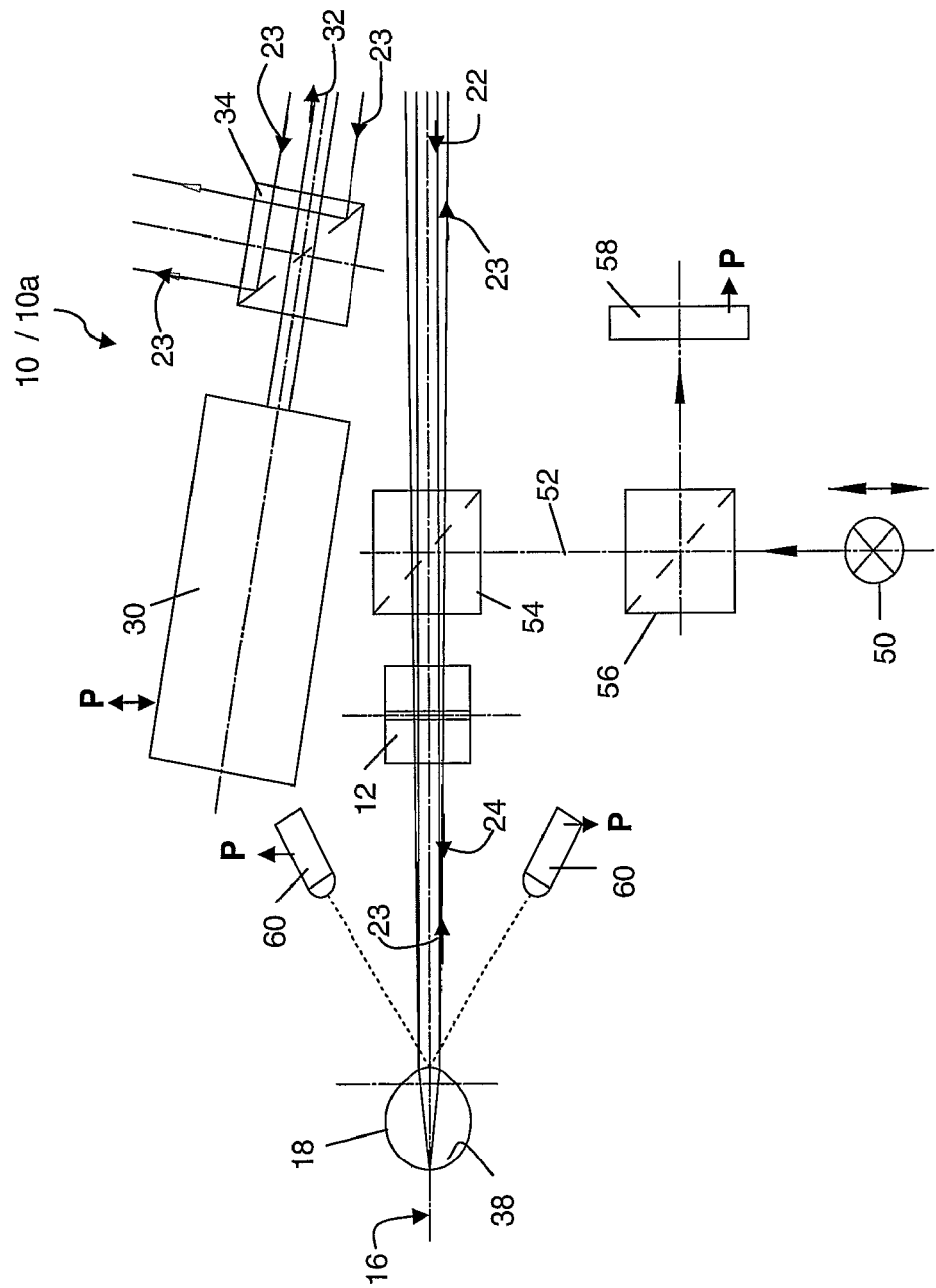
FIG. 4 is an enlarged partial detail of FIG. 3 showing some additional to features or refinements.

FIG. 4 shows some features that may be added to enhance the performance of the instrument 10 or variant 10a of FIGS. 1 and 2. A movable fixation target 50 is located on a gaze beam path 52 that is optically coupled by a first additional beam-splitter 54 into return beam path 23 and on optical axis 16. Fixation target 50 aligns the gaze or axis of the eye with optical axis 16 of the system and controls accommodation. A second additional beam-splitter 56 in gaze path 52 directs an image of eye 18 onto a CCD detector 58, allowing gaze direction and eye-alignment to be monitored since CCD detector 58 receives the ocular image via beam-splitters 54 and 56. Optical or acoustical distance sensors 60 can be used to (alternately or additionally) indicate when eye 18 appears to be axially aligned. Sensors 60, along with detector 58 if desired, can be connected to processor 49 (FIG. 3)—as indicted by arrows marked P—so that initiation of a measurement cycle can be automatic.

Figure 5:
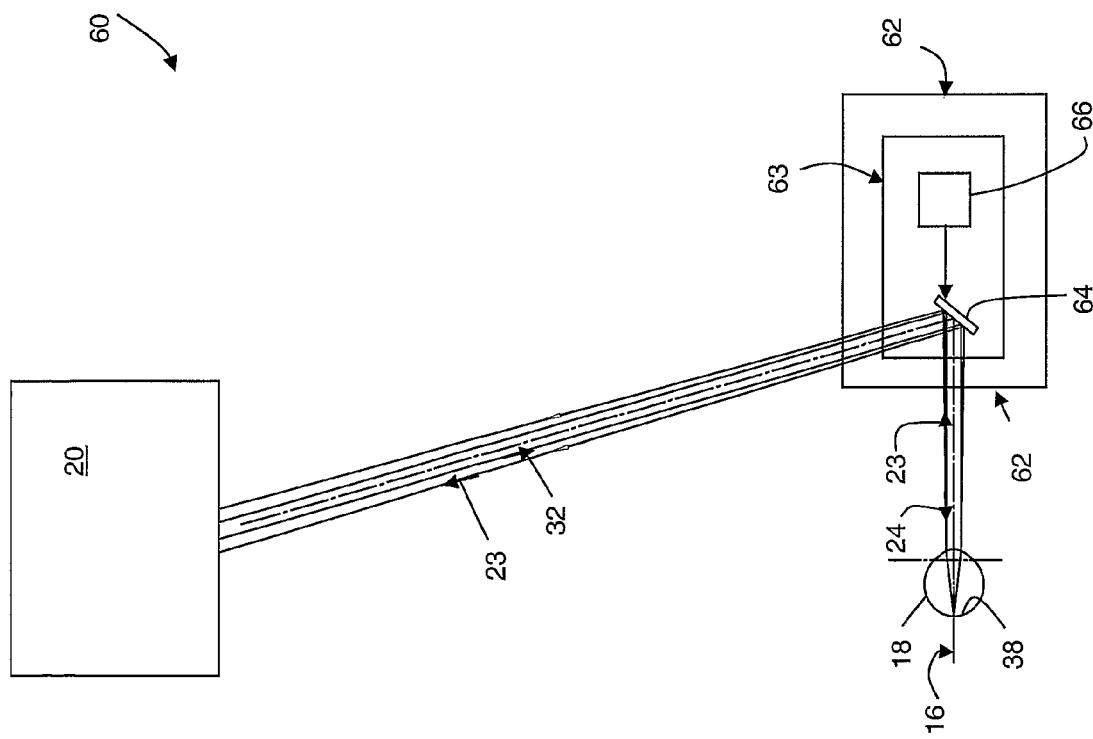
FIG. 5 is diagrammatic side elevation of an instrument that comprises the second example with a different optical configuration for beam steering from that of the first example of FIGS. 1-4.

FIG. 5 shows the optical layout of an instrument 60 that comprises the second example of the invention, which has a different deflector array 62 than that of the first example but, otherwise, may be substantially the same. The same reference numerals will therefore be used for elements of instrument 60 that are essentially the same as those of FIG. 1 or 2 of the first example. FIG. 5 is a plan view like that of FIGS. 3 and 4.

As in the first example, array 62 of instrument 60 comprises a row of beam deflector elements 63 but, in this case, each deflector element 63 comprises a mirror (or optionally a prism) 64 that can be tilted by an actuator 66. [It will be appreciated that, if mirrors 64 are fixedly located, instrument 60 will be substantially identical to instrument 10 of the first example in which the scanning function is performed by scanner means in source and detector unit 20, and/or by an LCD shutter 26 or LCD shutter 28 (see FIG. 1).] Actuator 66 can be a known solid-state device such as a barium titanate piezoelectric actuator. This allows instrument 60 of the second example to function quite differently from that of the first example, because each element 63 can be operated as a shutter or scanner. A number of different operational modes are envisaged.

First, many deflector elements 63 may be used in array 62 since their component mirrors 64 and actuators 66 can be made very small and mounted very precisely. They can be arranged much closer together than prisms 14 of array 12 in the first example, at least for sectors of the eye that are of particular interest. While light source, detector and processor unit 20 can be operated to scan the illuminating beam 22 along array 63 in a similar manner as described with reference to FIG. 3, it may be difficult to ensure that scanned beam 22 does not illuminate more than one of the closely spaced deflector mirrors at one time. Accordingly, actuators 66 can be operated to (i) 'correctly' angle only the intended mirror 64 to direct its interrogating beam 24 into eye 18 and (ii) 'incorrectly' angle nearby mirrors 64 to ensure that any beams that they generate are not directed into eye 18. This allows scanner 36/37 of FIG. 3 to effect coarse scanning leaving fine scanning to be undertaken by mirrors 64. [As will be understood from the description of the first example, a mirror that is correctly angled to direct an interrogating beam 22 in to eye 18 will also be correctly angled to direct return beam 23 from the retina 38 to the detector of unit 20.] Thus, in the operational mode just described, beam deflector elements 63 (comprising mirrors 64 and their actuators 66) can be operated like shutter 26 (or 28) of FIG. 1.

Second, the beam deflector elements 63 of a multiple element array 62 can be operated to perform some or all of the scanning functions of scanner mirror 36 of the first example. For example, instead of mounting small mirrors close together to finely interrogate eye areas of particular interest, a series of larger mirrors 64 can be successively illuminated by coarse scanning of illuminating beam 22 employing a coarse scanner in unit 20 (similar to mirror 36 described in the first example) and each illuminated mirror 64 can be moved by its actuator 66 to effect fine-scanning of interrogation beam 24 over a small range of angles.

Figure 6:
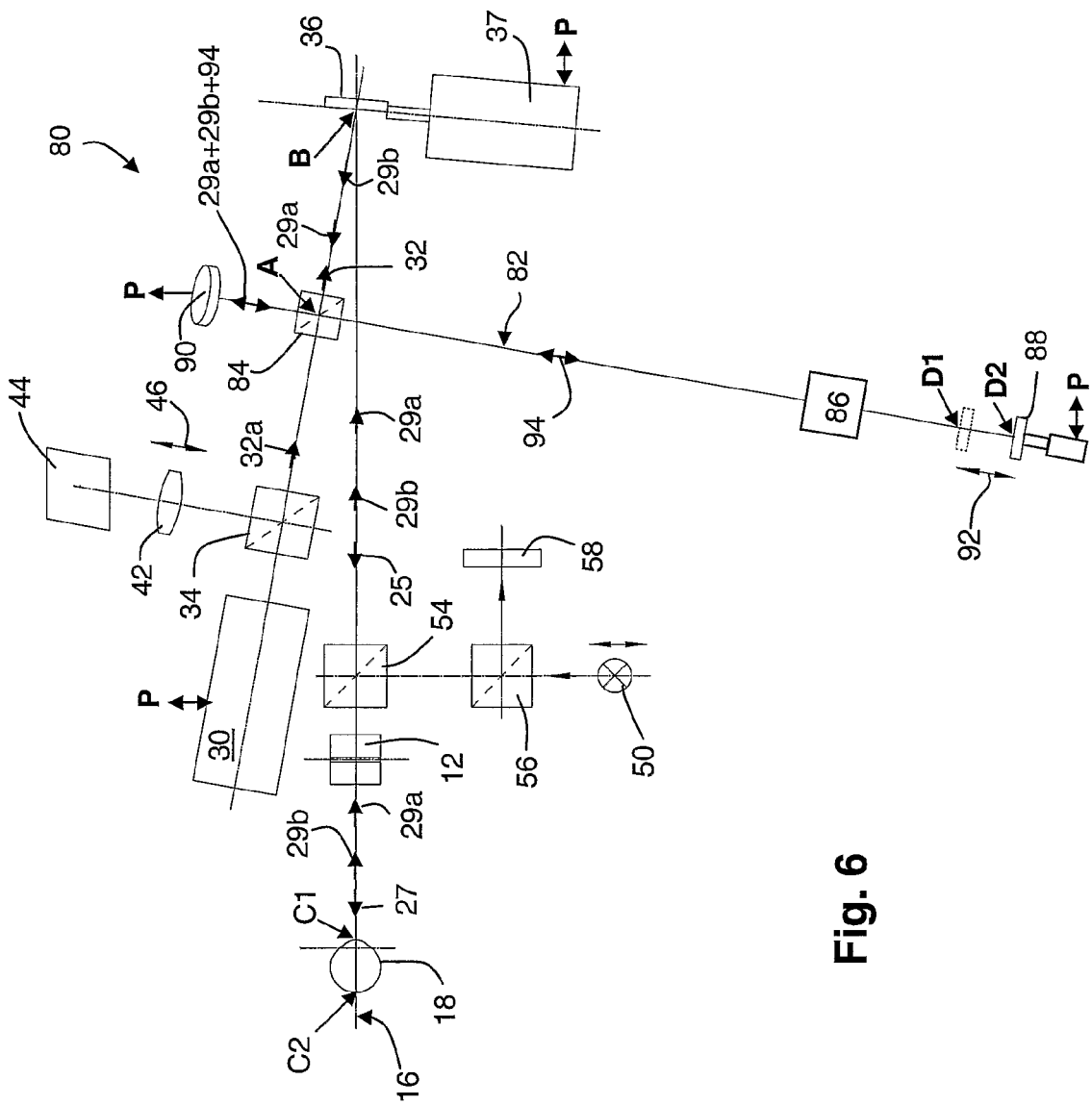
FIG. 6 is a diagrammatic side elevation of the instrument of FIG. 3 including means for measuring the length of the eye and/or the distance between elements thereof.

FIG. 6 illustrates an instrument 80 and a method that form the third exemplary embodiment of the invention and enable the measurement of eye length as well as wavefront aberrations and peripheral refraction. Instrument 80 incorporates the instrument of FIGS. 3 and 4 for measurement of wavefront aberration and peripheral refraction and adds thereto an interferrometer beam path 82 for the measurement of eye length. The same reference numerals will be used for those parts of instrument 80 that have substantially the same function as instrument 10 and will not be separately described here.

The interferrometer beam path 82 is arranged substantially at right angles to the source beam 32a that is emitted by light source 30. It comprises (i) an additional beam-splitter 84 arranged in beam 32 before scanning mirror 36, (ii) a dispersion compensation element 86, (iii) an additional moveable mirror 88 and (iv) an additional photo detector 90. As indicated by arrows 92, mirror 88 is moveable along beam path 82 toward and away from photo detector 90, by an actuator 93 under the control of processor 49 (FIG. 3). Preferably, actuator 93 is operated to reciprocate mirror 88 back and forth.

It will be assumed in what follows that the axial length of eye-system 18 is of interest, so axial illuminating, interrogating and return beams 25, 27 and 29 are those under consideration. In use, source beam 32a travels through additional beam-splitter 84 and is split at point A into two emerging beam portions, beam 32 which continues (as before described) to scanning mirror 36 and a reference beam 94 that is reflected by splitter 84 into beam path 82 on to reciprocating mirror 88 from which it is reflected back via point A to detector 90. Since the portion of interferometer path 82 between point A and detector 90 is also traveled by return beam portions 29a and 29b, which are reflected to detector 90 by splitter 84, reference beam 94 can interfere or beat with return beam portions 29a and 29b. It is of course necessary that the travel of mirror 88 during reciprocation is sufficient to cause interference between both return beam portions 29a and 29b. These interferences are detected by detector 90 and transmitted to processor 49 along with the precise position of mirror 88 (as indicated by arrows with the letter P. For convenience, it is assumed that interference with return beam portion 29a occurs when mirror 88 is at point D1 and that interference with return beam portion 29b occurs when mirror 88 is at point D2.

More specifically, the interference will appear if the optical distances [A, B, C1][A, D1] or [A, B, C2] and [A, D2] are equal. Since the relative, distance between D1 and D2 is accurately known from the mirror positions, the optical distances between points C1 and C2 are also known. The physical distance between cornea and retina surfaces can then be computed by using well known group refractive index values of ocular media to convert the optical distances into physical distances. Measurement accuracy can be improved by the use of the dispersion compensating element 86 into beam path 82, such devices being known in the art. It will be appreciated that, while the general optical techniques employed in additional beam path 82 to indicate eye length are not new (see, for example, the Schmid references identified above), the particular combination with instrument 10 is most useful, elegant and novel. However it will also be appreciated that other known techniques of optically indicating eye length may also be used separately or in combination with the optical characterization systems disclosed herein.

While a number of examples of the invention, along with a number of variants, have been described, it will be appreciated that many others are possible without departing from the scope of the invention as defined by the following claims. The specific terms and arrangements used in the examples have been for illustration rather than limitation.

The invention claimed is:

1. A method of optically characterising an eye-related optical system having a longitudinal optical axis, the method including the steps of:
   generating an interrogating light beam from each element of an array of discrete beam deflector elements, the array extending laterally from the optical axis,
   directing said light beam into the eye-related system at an angle relative to the optical axis which is at least in part determined by the lateral position of the element within said array,
   detecting a return beam from the eye-related system that is generated by said interrogating light beam and that is returned at said angle via said beam deflector element to detector means, and
   comparing said detected returned beam with one of said interrogating beam and an image of said interrogating beam to determine aberrations of the eye-related optical system at said angle.

2. A method according to claim 1, including the steps of:
   generating said interrogating beam by illuminating said beam deflector element with an illuminating beam emanating from a common point, said illuminating beam being deflected by said beam deflector element to form said interrogating beam, and
   returning said return beam to said common point for detection, such that each beam deflector element of the array can be illuminated by a respective illuminating beam to generate a respective interrogation beam at a respective angle and such that each return beam generated by said respective interrogation beam is returned to said common point for detection.

3. A method according to claim 2 including the step of:
   simultaneously illuminating a plurality of beam deflector elements so as to simultaneously generate a corresponding plurality of return beams,
   differentially encoding said plurality of return beams, and
   separately detecting each return beam using said encoding.

4. A method according to claim 2, including the step of:
   simultaneously illuminating a plurality of beam deflector elements so as to simultaneously generate a corresponding plurality of interrogating beams, and
   selectively gating said plurality of interrogating beams to permit passage of fewer interrogating beams into the eye-related system.

5. A method according to claim 2, including the step of:
   simultaneously directing a plurality of illuminating beams at a plurality of beam deflector elements, and
   selectively gating said plurality of illuminating beams to selectively illuminate said plurality of beam deflector elements.

6. A method according to claim 2, including the step of:
   moving at least one of said beam deflector elements to change the angle of the interrogating beam generated by said at least one of said elements.

7. A method according to claim 2, including the step of:
   generating a narrow source beam from a light source to form said common point,
   directing each return beam to return along the source beam, and
   diverting at least a portion of each return beam from said source beam for detection.

8. A method according to claim 7, including the step of:
   moving the illuminating beam over the array of beam deflector elements to generate the interrogating light beams and the respective return beams in an ordered manner.

9. A method according to claim 8, including the step of:
   employing scanning means comprising a moving mirror,
   illuminating said moving mirror with the source beam to form said common point on said mirror and so that said illuminating beams are formed and scanned therefrom,
   directing each return beam back along each scanned illuminating beam to the mirror so that each return beam is directed by the mirror back along the source beam for detection.

10. A method according to claim 7, including the step of:
    sequentially scanning the illuminating beam over beam deflector elements of said array to sequentially generate the interrogation and return beams, and
    sequentially detecting the return beams thereby generated.

11. A method according to claim 7, including the step of:
    detecting each return beam after separation from said source beam by focusing it to form an image on a photo detector to generate a corresponding output signal from the photo detector,
    varying the focus of the image through a range of focii, and
    recording the output signal for comparison with a corresponding recorded image representative of the respective interrogating beam.

12. A method according to claim 7, wherein the eye-related optical system is one of a natural human eye and a model thereof having a cornea surface and a retina surface such that each return beam has a first component indicative of reflection from the cornea and a second component indicative of reflection from the retina, the method including the following additional steps:
    diverting a portion of each returned beam from said source beam into an interferometer beam path that has an interference detector at one end and a reflector at the other end which can be reciprocated to shorten or lengthen the interferometer beam path,
    diverting a portion of said source beam into said interferometer beam path to form a reference beam,
    reciprocating said reflector to vary the length of said interferometer beam path so as to cause a first interference between said reference beam and said first component of the return beam in said path at a first position of said reflector, said first interference being detected by said interference detector, reciprocating said reflector to vary the length of said interferometer beam path so as to cause a second interference between said reference beam and said second component of the return beam in said path at a second position of said reflector, said second interference being detected by said interference detector, and determining the distance between said first and second positions, said distance being indicative of the physical distance between the cornea and the retina of the eye along the path of the respective return beam.

13. A method according to claim 1 wherein the eye-related system is an eye of a myopic human patient and wherein the method includes the steps of:

determining that the eye is aligned with the optical axis, and then performing the steps set out in claim 1 to determine peripheral eye aberrations at angles of at least 30 degrees relative to the optical axis within a time period short enough to avoid significant inadvertent eye movement.

14. An instrument for use in optically characterizing an eye-related optical system with respect to an optical axis, the instrument including:

an array of discrete beam deflector elements extending laterally with respect to the optical axis, an interrogating light beam being generated from each of said elements into the eye-related system at an angle with respect to the optical axis that is at least partially determined by the location of the array element within said array, wherein in use, a return light beam generated by reflection or back-scattering of a respective interrogating beam from within the eye-related system is returned via the respective beam deflector element, a detector is provided for detecting each return beam, said detector having a detector output for transmitting an output signal indicative of each said detected return beam, and a processor is in communication with said detector to receive said output signal and is adapted to compare said output signal with a signal representative of the interrogating beams and is further adapted to generate a processor output indicative of aberrations of the paths within the eye-related system traversed by the return beams.

15. An instrument according to claim 14, including:

a light source adapted to generate and propagate a source light beam along a source beam path, an illuminator optically connected to said source beam path and adapted to generate and direct an illuminating beam at said array to illuminate said beam deflector elements and to thereby generate said interrogating beams from said elements, the instrument being such that, when the instrument is in use, each return beam is returned via said illuminating beam to said source beam, a beam splitter within said source beam path adapted to divert a least portion of each return beam in said source path to said detector.

16. An instrument according to claim 15, wherein:

said illuminator includes a beam scanner adapted to scan said illuminating beam over the beam deflector elements of the array so as to generate a succession of interrogation beams and return beams.

17. An instrument according to claim 15, wherein:

said illuminator is adapted to illuminate more than one beam deflector element at once, an electronic shutter is provided and positioned before the array, said shutter being adapted to control which beam deflector elements are illuminated by said illuminator.

18. An instrument according to claim 15, wherein:

said illuminator is adapted to illuminate more than one beam deflector element at once, an electronic shutter is provided after the array, said shutter being adapted to determine the interrogation beams that are able to enter the eye-related system.

19. An instrument according to claim 15, including:

an encoder adapted to differentially encode a plurality of return beams to facilitate separate detection thereof by said detector.

20. An instrument according to claim 14 wherein:

a moveable beam deflector element is mounted for movement relative to the array, an actuator is linked to said moveable deflector element for moving said element, said actuator is connected to said processor for operation thereby so as to selectively change the angle of return beams generated from said moveable element.

21. An instrument according to claim 14 wherein the eye-related optical system is a natural human eye or a model thereof, the eye having a cornea surface and a retina surface such that each return beam has a first component indicative of reflection from the cornea and a second component indicative of reflection from the retina, wherein:

the instrument has an interferometer beam path that intersects said source beam path, a second beam splitter is located in the intersection of said source path and said interferometer beam path and is adapted to divert a portion of the source beam into said interferometer beam path as a reference beam and to divert portion of a return beam travelling in said source beam path into said interferometer beam path, an interference detector is arranged at one end of said interferometer beam path and is connected to said processor so as to signal the processor when an interference between said reference beam and said return beam in said source path is detected, a reflector is arranged at the other end of said interferometer beam path, a reflector actuator is connected to said reflector and to said processor for reciprocating the reflector along said interferometer beam path under the control of the processor so as to change the effective length of said interferometer beam path, and during operation, interference between said first component of the return beam and the reference beam is signalled to the processor together with a first position of the reflector actuator, and interference between said second component of the return beam and the reference beam is signalled to the processor together with a second position of the reflector actuator, to thereby enable said processor to compute the distance between the cornea and the retina of the eye along the path of the return beam within the eye.

* * * * *